United States Patent [19]

Heilmann et al.

[11] Patent Number: 4,556,723

[45] Date of Patent: Dec. 3, 1985

[54] PROCESS FOR THE PRODUCTION OF ACYLOINS

[75] Inventors: Steven M. Heilmann, North St. Paul; Larry R. Krepski, White Bear Lake; Jerald K. Rasmussen, Stillwater, all of Minn.

[73] Assignee: Minnesota Mining and Manufacturing Company, St. Paul, Minn.

[21] Appl. No.: 712,228

[22] Filed: Mar. 15, 1985

Related U.S. Application Data

[62] Division of Ser. No. 468,719, Feb. 22, 1983.

[51] Int. Cl.$^4$ ............................ C07F 7/08; C07F 7/10; C07F 7/18
[52] U.S. Cl. .................................................. 556/413
[58] Field of Search ......................................... 556/413

[56] References Cited

U.S. PATENT DOCUMENTS 3,946,060  3/1976  Metcalf et al. ...................... 556/413
4,088,668  5/1978  Metcalf et al. .................. 556/413 X

*Primary Examiner*—Paul F. Shaver
*Attorney, Agent, or Firm*—Donald M. Sell; James A. Smith; David L. Weinstein

[57] ABSTRACT

Process for the production of an acyloin comprising the steps of:
  A. reacting a Grignard reagent with silylated cyanohydrin,
  B. treating the reaction product of step A with aqueous acid, and
  C. recovering the resulting acyloin.

Acyloins thus formed are useful as photoinitiators for initiation of free radical polymerization reactions.

1 Claim, No Drawings

PROCESS FOR THE PRODUCTION OF ACYLOINS

This is a division of application Ser. No. 468,719 filed Feb. 22, 1983.

This invention relates to acyloins and the preparation thereof.

Acyloins (alpha-hydroxyketones) have been known for some time to be useful as photoinitiators for effecting free radical addition polymerization reactions. An example of this utility is disclosed in U.S. Pat. No. 2,367,661. Although acyloins are adequate photoinitiators for many polymerization processes, U.S. Pat. No. 2,448,828 discloses that a superior photoinitiator results from the conversion of a given acyloin to an acyloin ether. Acyloin ethers generally exhibit increased efficiency as photoinitiators compared to acyloins and reduce the time required for substantial polymerization of ethylenically unsaturated organic compounds without sacrificing the quality of the polymers produced.

Although several methods have been developed for the synthesis of acyloins, it generally can be stated that the best results, in terms of reaction yields, have been achieved in synthesizing the so-called "symmetrical acyloins", in which the substituents X and Y in structural formula I below are the same.

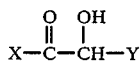
                                                                     I Certain acyloins which contain both aromatic and aliphatic groups, i.e., the so-called "mixed acyloins", in which X and Y of formula I are different, are considered to be superior photoinitiators compared to the simpler aforementioned symmetrical acyloins or their ether derivatives. The mixed acyloins are considerably more difficult to prepare in high yield than are the symmetrical acyloins.

U.S. Pat. No. 4,318,791 teaches the preparation of mixed acyloins using the three-step procedure shown below in Method 1, where Ar represents an aryl radical and R and R' represent monovalent aliphatic, cycloaliphatic, or araliphatic radicals.

Method 1

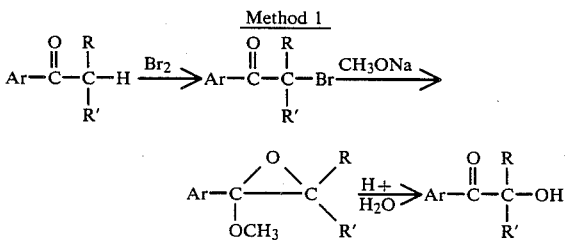

No yields are stated in the patent. The method not only has the disadvantage of requiring three separate reactions, but the starting material is also a deoxyacyloin compound which is not always commercially available or capable of simple preparation. Moreover, some elimination of water, leading to olefin by-products by a side reaction, may be expected to occur during the hydrolysis step. This side reaction can be expected to be particularly troublesome when both R and R' are not hydrogen.

A more general synthesis of mixed acyloins, shown below in Method 2, involves conversion of an aldehyde or ketone into its cyanohydrin derivative, followed by reaction with a Grignard reagent, and subsequent hydrolysis. The following reaction sequence is described in *Organic Reactions,* Volume IV, John Wiley & Sons, Inc., New York, (1948) p. 289-290. The yields obtained by this process are only 20-45%. Although, in theory, the process of Method 2 requires two equivalents of the Grignard reagent, ArMgX, in practice it is often necessary to use substantially more than two equivalents of the reagent in order to obtain adequate yields.

Method 2

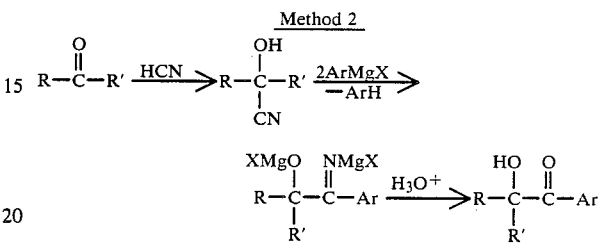

Improved yields can be obtained by blocking the hydroxyl group of the cyanohydrin with an ethoxyethyl group (See I. Elphimoff-Felkin, Bull. Soc. Chim. Fr., (1955), 784) or a tetrahydropyranyl ether group (See I. Elphimoff-Felkin and M. Verrier, Bull. Soc. Chim. Fr., (1967), 1047). However, the blocking reactions themselves result in variable yield, and the subsequent removal of the ethoxyethyl group or tetrahydropyranyl ether group requires refluxing under acidic conditions. Refluxing under these conditions can lead to the elimination side reaction described above.

X. Creary and C. C. Geiger, J. Am. Chem. Soc., 104, 4151 (1982), disclose the reaction of the trimethylsilylated cyanohydrin of norcamphor with tertiary-butyllithium to produce an acyloin in moderate yield, i.e., about 40 percent. The following reaction is set forth therein:

Method 3

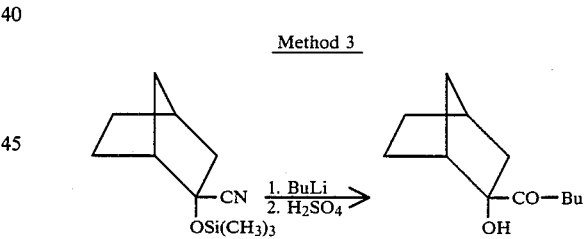

wherein Bu is the tertiary-butyl radical.

The method employed in the foregoing reaction is undesirable for these reasons:

(1) The reaction requires very low temperature, i.e., −78° C.

(2) The t-butyllithium reagent is added to the trimethylsilylated cyanohydrin. The addition of an oxygen-sensitive, moisture-sensitive reagent, i.e. t-butyllithium, to another less sensitive reagent is known as an "inverse addition". This is in contrast to the more desirable "normal addition" process wherein the more reactive, more difficult-to-handle reagent is prepared and further reacted in the same vessel.

(3) Organolithium reagents are, in general, more expensive than Grignard reagents and are less readily available commercially.

(4) The process shown is suitable only for sterically hindered organolithium reagents such as t-butyllithium.

The present invention provides a method for producing an acyloin, comprising the steps of:
A. reacting a Grignard reagent with a silylated cyanohydrin,
B. treating the reaction product of step A with aqueous acid, and
C. recovering the resulting acyloin.

The process of this invention is more efficient and generally results in higher yields, e.g., greater than 60%, of acyloin compounds than the methods which have been previously employed. Acyloins prepared by this method are useful as photoinitiators for effecting polymerization reactions.

Preparation of the Grignard reagent is well-known in the art and, for example, is discussed in detail in M. S. Kharasch and O. Reinmuth, *Grignard Reactions of Nonmetallic Substances*, Prentice-Hall, Englewood Cliffs, N.J. (1954), Chapter 2. In general, an organohalogen compound is allowed to react with magnesium in an anhydrous solvent to yield the organomagnesium halide, i.e., the Grignard reagent. Useful solvents for preparing Grignard reagents include benzene, toluene, diethyl ether, tetrahydrofuran, diisopropyl ether, and methyl t-butyl ether, with the ether solvents being preferred. The process for forming the Grignard reagent is generally exothermic; consequently, the organohalogen compound is generally dissolved in the solvent and added portion-wise or dropwise to the magnesium metal immersed in the same solvent such that mild refluxing of the solvent occurs, thus mediating the exothermicity of the reaction. The mixture can be refluxed for about 1 to 2 hours to ensure complete reaction of all the added organohalogen compound. The reaction mixture should then be allowed to cool to room temperature (25° C.) whereupon it can then be used directly in the process of the invention.

Grignard reagents that are preferred for use in the process of this invention can be represented by the formula:

$$R^1MgX$$

wherein
R$^1$ is an alkyl radical, e.g., containing 1 to 20 carbon atoms, an aralkyl radical, e.g., containing 7 to 12 carbon atoms, or an aryl radical, e.g., containing 6 to 14 carbon atoms, said radicals being optionally substituted with one or more hetero atoms selected from chloro, fluoro, tertiary amino nitrogen and ether oxygen, and
X is chloro, bromo or iodo.

Representative examples of Grignard reagents that are suitable for use in the process of this invention are methylmagnesium chloride, ethylmagnesium iodide, ethylmagnesium bromide, n-propylmagnesium chloride, n-butylmagnesium chloride, n-hexylmagnesium bromide, tetramethylenedimagnesium dibromide, n-octylmagnesium chloride, phenylmagnesium bromide, p-chlorophenylmagnesium bromide, and phenylmagnesium chloride.

Silylated cyanohydrin compounds useful in this invention are well-known in the art and can be prepared by reacting an aldehyde or ketone with a silyl cyanide, optionally in the presence of a catalyst. The reaction between the silyl cyanide and the aldehyde or ketone can take place in the absence or presence of solvent. Examples of solvents useful for the reaction are polar aprotic solvents, such as acetonitrile, N,N-dimethylformamide, N,N-dimethylacetamide and N-methylpyrrolidone, or non-polar aprotic solvents such as benzene, toluene, chloroform, methylene chloride, hexane, and pentane. Solvents that are unsuitable for the reaction are those which would react with the silyl cyanide reactant or the silylated cyanohydrin product. These include water and alcoholic solvents. The reaction may be conducted in the presence of catalysts, such as zinc cyanide and zinc iodide, to hasten formation of the silylated cyanohydrin product.

Although the trimethylsilyl cyanide reagent used in this invention is commercially available, methods are known for generating the trimethylsilyl cyanide reagent in situ. In J. K. Rasmussen and S. M. Heilmann, *Synthesis*, (1978), pp. 219–221, a method for synthesizing silylated cyanohydrins is disclosed. This method involves reacting an aldehyde or ketone with chlorotrimethylsilane and potassium cyanide in a solvent such as acetonitrile or N,N-dimethylformamide. The reaction is accomplished by adding the carbonyl compound (0.1 mol) to a stirred suspension of potassium cyanide (0.3 mol) in solvent (20 ml), trimethylsilyl chloride (0.16 mol) and, optionally, zinc iodide (0.05 g). The mixture is refluxed gently and monitored by gas liquid chromatography. On completion, the reaction mixture is filtered, the filter cake washed with dry solvent, and the combined filtrates concentrated in vacuo. Distillation at reduced pressure affords pure silylated cyanohydrins.

Silylated cyanohydrins that are preferred for use in the process of this invention can be represented by the formula:

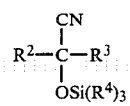

wherein
R$^2$ and R$^3$ are independently hydrogen, an alkyl radical, e.g., containing 1 to 20 carbon atoms, an aralkyl radical, e.g., containing 7 to 12 carbon atoms, or an aryl radical, e.g., containing 6 to 14 carbon atoms, said radicals being optionally substituted with one or more hetero atoms selected from halogen, tertiary amino nitrogen, or ether oxygen, and
R$^4$ is an alkyl radical, e.g., containing 1 to 6 carbon atoms, an aralkyl radical, e.g., containing 7 to 12 carbon atoms, or an aryl radical, e.g., containing 6 to 14 carbon atoms.

Choice of the R$^4$ groups is not particularly important since those groups are not retained in the final acyloin product. A preferred R$^4$ group is methyl, because the trimethylsilyl cyanide reagent is commercially available or can be formed in situ as described above.

Examples of silylated cyanohydrins that are suitable for use in the process of this invention are the silylated cyanohydrins of acetone, methyl ethyl ketone, cyclohexanone, cyclohexanecarboxaldehyde, butyraldehyde, camphor, benzaldehyde, acetophenone, p-anisaldehyde, p-tolualdehyde, m-dimethylaminobenzaldehyde, o-chlorobenzaldehyde, benzophenone, phenylacetaldehyde, deoxybenzoin, pivaldehyde, pyridine-2-carboxaldehyde, p-nitrobenzaldehyde, fluorenone, and cyclododecanone.

The reaction of the silylated cyanohydrin compound with the Grignard reagent can be accomplished by adding a solution of the silylated cyanohydrin compound to the Grignard reagent solution. It is preferred that the solution of silylated cyanohydrin compound be added dropwise to the Grignard reagent over a period of about one-half to one hour. The reaction, which is depicted by Equation (1) and results in the magnesium salt of the alpha-silyloxy imine, which is believed novel, per se, is mildly exothermic—less so than the reaction wherein the Grignard reagent is prepared. Consequently, external cooling of the reaction mixture can usually be avoided.

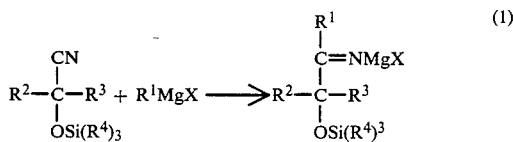

wherein $R^1$, $R^2$, $R^3$ and $R^4$ are as defined above.

Solvents that are appropriate to dissolve the silylated cyanohydrin reactant are the solvents which are suitable for use in the preparation of the Grignard reagent. After the addition of the solution of the silylated cyanohydrin compound has been completed, the reaction mixture can be refluxed to ensure that all the silylated cyanohydrin has reacted. Preferably, the reaction mixture is refluxed for an additional 1 to 2 hours.

Generally, 0 to 200% molar excess of the Grignard reagent, with a preferred excess of 0 to 100%, and a more preferred excess of 5 to 25%, can be employed. Use of substantial excesses of Grignard reagent results in diminished yields and much more complicated reaction product mixtures.

The acid treatment or hydrolysis step in the process of this invention involves treatment of the reaction product of Equation (1) with aqueous acid. This step can be accomplished by pouring the reaction product into water containing at least one equivalent of acid.

Although only one equivalent of acid can be used, it is generally desirable to utilize a substantial excess, e.g., 10 to 20 equivalents, to increase the rate of the hydrolysis reaction and, in addition, to react with any residual magnesium metal that may be present. Both inorganic and organic acids can be used. Examples of acids that are useful in this step of the process are hydrochloric acid, sulfuric acid, nitric acid, phosphoric acid, acetic acid, trifluoroacetic acid, and methanesulfonic acid, with hydrochloric acid or sulfuric acid being preferred.

As depicted by Equation (2), the hydrolysis reaction is believed to take place in a stepwise fashion.

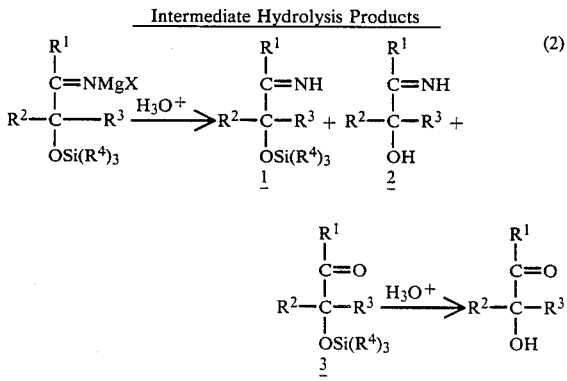

The first step, involving generation of the "Intermediate Hydrolysis Products", takes place rapidly, and a mixture of these partially hydrolyzed products results from mixing, e.g. by shaking in a separatory funnel, the reaction solution obtained by reacting the Grignard reagent with the silylated cyanohydrin. Because the Intermediate Hydrolysis Products are different, further reaction workup is preferably divided into two portions at this point by separating the two layers. The aqueous acidic layer will contain any Intermediate Hydrolysis Products that contain an imine functional group as in 1 and 2, because the basic imine group will be protonated, forming a salt, which, is soluble in water. The organic layer will contain water insoluble Intermediate Hydrolysis Products such as 3, along with any completely hydrolyzed product.

The aqueous acid layer can be allowed to stand at room temperature overnight, e.g. about 12 to 16 hours. The material that separates from the aqueous layer can be collected as a portion of the acyloin product. The organic solvent can be distilled from the organic layer and replaced with an equal volume of a water-miscible solvent, examples of which are methanol, ethanol, tetrahydrofuran, acetone, and dioxane. These solvents are compatible with acids, especially aqueous acids such as hydrochloric acid and sulfuric acid, the preferred acids. The resulting solution can be allowed to stand at room temperature overnight to effect the final hydrolysis. The solvent can then be removed by distillation, leaving a residue which can then be combined with material that had separated from the aqueous layer. In the case where the material is a solid, the crude acyloin product can be recrystallized from a suitable solvent to obtain the acyloin product in pure form. Solvents that are useful for recrystallization include the common organic solvents such as ethanol, methanol, hexane, heptane, ethyl acetate, acetone, and mixtures thereof. Acyloin products that are liquids can be purified by distillation, preferably under reduced pressure.

Acyloins produced by this invention can be used as photoinitiators in the preparation of polymers, following, for example, the procedure of U.S. Pat. No. 2,367,661.

The invention is further illustrated by the following non-limiting examples.

EXAMPLE 1

Preparation of 4'-Fluorobenzoin

A. Preparation of the Trimethylsilylated Cyanohydrin of Benzaldehyde

In a one liter, three-necked, round-bottomed flask equipped with a mechanical stirrer, a reflux condenser fitted with a nitrogen inlet tube, and a rubber septum were placed 97.5 grams (1.5 moles) of finely ground potassium cyanide which had been previously passed through a 30 sieve and dried at 115° C. at 0.5 Torr for 24 hours, 100 mL of acetonitrile which had been previously dried over 4 A molecular sieves, 81.45 grams (0.75 mole, 95.2 mL) of chlorotrimethylsilane, 53 grams (0.5 mole) of benzaldehyde, and 0.5 gram (0.4 mmole) of zinc cyanide catalyst (available from Matheson, Coleman, and Bell Manufacturing Chemists, Norwood, Ohio). The reaction was conducted under a blanket of dry nitrogen. Stirring was begun, and the temperature was raised to maintain gentle refluxing. After 21 hours, the reaction was complete as evidenced by absence of benzaldehyde in the gas liquid chromatographic analysis of the reaction mixture. The reaction mixture was cooled and filtered with suction. The filter cake was washed twice with 50 mL of acetonitrile, and the combined filtrates were concentrated on a rotary evaporator. The residue was distilled at 93°–95° C. at 1.75 Torr, and the distilled product was found to weigh 84.0 grams (95% yield). Spectral analyses confirmed the the product as being trimethylsilylated cyanohydrin.

B. Preparation of 4-Fluorophenylmagnesium Bromide

In a one liter, three-necked, round-bottomed flask equipped with a mechanical stirrer and a reflux condenser were placed 1.34 grams (0.055 gram-atoms) of magnesium metal turnings and 10 mL of anhydrous diethyl ether. A solution of 8.75 grams (0.05 mole) 4-bromofluorobenzene dissolved in 90 mL of diethyl ether, was added dropwise at such a rate that gentle refluxing of the solvent occurred. After the addition of 4-bromofluorobenzene, which required about 20 minutes, the reaction mixture, which was brown in color, was refluxed for an additional hour.

C. Reaction of the Trimethylsilylated Cyanohydrin of Benzaldehyde with 4-Fluorophenylmagnesium Bromide To the above-prepared Grignard reagent of Paragraph B was dropwise added, over a period of one hour, 9.0 grams (0.044 mole) of the above-prepared trimethylsilylated cyanohydrin dissolved in 75 mL of diethyl ether. Stirring was continued an additional two hours.

D. Hydrolysis of the Reaction Product

The reaction product of the Paragraph C was poured into a separatory funnel containing 20 mL of concentrated sulfuric acid dissolved in 500 mL of cold water. Two layers formed and were separated. The ether layer was extracted once with 100 mL of 10% aqueous hydrochloric acid solution, and the aqueous solutions were combined. The combined aqueous solution, upon standing overnight at room temperature, deposited a crystalline solid. Filtration and drying resulted in 6.3 grams (62% yield) of 4'-fluorobenzoin, shown to be pure by thin layer chromatographic analysis (silica gel plate developed in the usual manner with ethyl acetate/hexane, ratio 30:70, v:v).

The ether solution was washed with saturated aqueous sodium chloride, dried over anhydrous magnesium sulfate, and the ether solvent evaporated, leaving 6.51 grams of a colorless oil. $^1$H-NMR indicated the oil to consist of a mixture of the desired benzoin and the silylated benzoin (molar ratio 30:70). This mixture was dissolved in 75 mL of methanol. One mL of 10% aqueous hydrochloric acid solution was added, and the solution was allowed to stand at room temperature (25° C.) overnight. The solvent was then evaporated to leave 5.4 grams of a tan solid. This material was combined with the material from the filtration step and recrystallized twice from aqueous methanol to yield 8.0 grams (79% yield) of 4'-fluorobenzoin, m.p. 108°–109° C. The structure of the 4'-fluorobenzoin compound was confirmed by infrared and $^1$H-NMR spectroscopy, and by elemental analysis.

EXAMPLES 2–7

The procedure of Example 1 was employed to synthesize the acyloin compounds listed in Table I.

TABLE I

| Example | Acyloin prepared | Stoichiometric excess of Grignard reagent$^a$ (%) | Yield$^b$ (%) | Acyloin melting range (°C.) |
| --- | --- | --- | --- | --- |
| 2 | 4-methylbenzoin | 10 | 69 | 117–117.5 |
| 3 | 4-methylbenzoin | 150 | 47 | — |
| 4 | 4-chlorobenzoin | 20 | 83 | 115–116 |
| 5 | α-hydroxycyclohexyl phenyl ketone | 20 | 61 | 46–48 |
| 6$^c$ | 2-cyclohexyl-2-hydroxyacetophenone | 10 | 73 | 89.5–90 |
| 7 | 4-methoxybenzoin | 150 | 38 | 87–89 |

$^a$The Grignard reagent was phenylmagnesium bromide.
$^b$The yield is based on the amount of silylated cyanohydrin.
$^c$This compound had been previously reported as an oil, and, therefore, further corroboration of the structure was obtained from the spectral characteristics of the sample and satisfactory elemental analysis.

From the foregoing examples, it is apparent that the process of the present invention is capable of producing acyloins in yields higher than those attainable by processes currently employed in the art.

Various modifications and alterations of this invention become apparent to those skilled in the art without departing in the spirit and scope of this invention, and it should be understood that this invention is not to be limited to the illustrative embodiments set forth herein.

What is claimed is:

1. A product represented by the formula

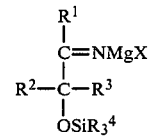

wherein

R$^1$ is an alkyl radical, an aralkyl radical, or an aryl radical, and

R$^2$ and R$^3$ are independently hydrogen, an alkyl radical, an aralkyl radical, or an aryl radical, R$^4$ is an alkyl radical, an aralykyl radical, or an aryl radical, and X is chloro, bromo, or iodo.

* * * * *